United States Patent [19]

Sannan et al.

[11] 4,267,313
[45] May 12, 1981

[54] SACCHARIDE DERIVATIVE HAVING UREIDO GROUP

[75] Inventors: Takanori Sannan, Tokyo; Shojiro Horiguchi, Hoya, both of Japan

[73] Assignee: Dainichiseika Color & Chemicals Mfg. Co. Ltd., Tokyo, Japan

[21] Appl. No.: 109,031

[22] Filed: Jan. 2, 1980

[30] Foreign Application Priority Data

Feb. 16, 1979 [JP] Japan .................................. 54-16217

[51] Int. Cl.$^3$ ............................................... C07H 5/06
[52] U.S. Cl. ....................................... 536/18; 536/20; 536/53
[58] Field of Search ............................. 536/20, 53, 18

[56] References Cited

U.S. PATENT DOCUMENTS

| | | | |
|---|---|---|---|
| 2,527,839 | 10/1950 | Morton | 536/53 |
| 2,612,497 | 9/1952 | Meijer | 536/53 |
| 3,577,406 | 5/1971 | Hessler | 536/53 |
| 4,059,097 | 11/1977 | Casey | 536/20 |
| 4,195,175 | 3/1980 | Peniston et al. | 536/20 |

*Primary Examiner*—Johnnie R. Brown
*Attorney, Agent, or Firm*—Oblon, Fisher, Spivak, McClelland & Maier

[57] ABSTRACT

A saccharide derivative having ureido group having 100 to 1% of N-carbamoyl-D-glucosamine unit, 0 to 90% of D-glucosamine unit and 0 to 70% of N-acetyl-D-glucosamine unit. The saccharide derivatives having ureido group can be used as fabricated products, an adhesive agent, a bonding agent, a processing agent, a coating agent, a soil improver, a fertilizer coating material, a water swellable material and a water absorbent.

2 Claims, No Drawings

SACCHARIDE DERIVATIVE HAVING UREIDO GROUP

BACKGROUND OF THE INVENTION

1. FIELD OF THE INVENTION

The present invention relates to novel derivatives of natural polysaccharides and a process for producing the same.

More particularly, it relates to novel compounds obtained by introducing carbamoyl group into a hydrolyzed product of chitin and a process for introducing carbamoyl group.

2. DESCRIPTION OF THE PRIOR ARTS

The chitin is a natural macromolecular compound having N-acetyl-D-glucosamine units as main units and is obtained by isolating from crustacea or algae. The chitin has unique characteristics such as excellent biodegradability which are not found in the other synthetic macromolecular compounds. The source of chitin is relatively abundant. For example, chitin can be obtained from integuments of crab, lobster and euphausia whose production is remarkably increased year by year. However, most of these sources have been wasted without any use, because the utility of chitin has not been developed.

The inventors have studied to obtain useful derivatives of chitin and to utilize effectively chitin, from the above-mentioned viewpoints.

SUMMARY OF THE INVENTION

It is an object of the present invention to obtain useful derivatives of chitin isolated from integuments of crab, lobster and euphausia, etc.

The saccharide derivatives having ureido group as carbamoylamino group of the present invention are obtained by hydrolyzing chitin to obtain chitosan or its analog thereof and converting amino group of chitosan or analog into carbamoylamino group. The saccharide derivatives having ureido group can be utilized in various fields.

The saccharide derivatives having ureido group of the present invention comprise about 100 to 1% of N-carbamoyl-D-glucosamine unit, about 0 to 90% of D-glucosamine unit and 0 to 70% of N-acetyl-D-glucosamine unit.

The saccharide derivatives having ureido group of the present invention can be produced by hydrolyzing chitin to obtain chitosan or its analog and reacting chitosan or its analog with a compound selected from the group consisting of cyanic acid, isocyanic acid, salts thereof or urea, biuret or triuret which is converted into isocyanic acid by heating.

DETAILED DESCRIPTION OF THE PREFERRED EMBODIMENTS

Degree of deacetylation and degree of polymerization of chitosan or its analog are not critical. Any chitosan analogs can be used. It is preferable to use the chitosan analogs whose degree of deacetylation is in a range of 100 to 30% preferably about 80% and whose viscosity as an aqueous solution of 1% of chitosan concentration and 1% of acetic acid concentration is in a range of 10 to 2,000 cps.

The acid used in the present invention can be acids which dissolve or highly swell chitosans such as organic acids e.g. formic acid, acetic acid, pyruvic acid and lactic acid and inorganic acids e.g. hydrochloric acid. It is optimum to use acetic acid.

The agents for carbamoylation as the characteristic feature of the present invention can be cyanic acid, isocyanic acid or salts thereof such as sodium or potassium salts; or urea, biuret or triuret which is converted into isocyanic acid by heating.

It is optimum to use sodium isocyanate.

The saccharide derivative having ureido group of the present invention can be produced as follows.

The chitosan or its analog is dispersed in water and an acid is added at a molar ratio of 0.1 to 5 preferably about 1.2 based on amino group of chitosan or its analog to prepare an aqueous solution of acid salt of chitosan or its analog. The agent for carbamoylation is added to the solution at a molar ratio of 0.01 to 5 based on amino group of chitosan or its analog and the mixture is stirred at 0° to 100° C. for 5 minutes to 24 hours. After the specific time, pH of the reaction mixture is tested. When pH of the reaction mixture is lower than 8, pH of the reaction mixture is increased to higher than 8 preferably about 9 by adding a base such as an alkali metal carbonate such as sodium carbonate and potassium carbonate or an alkali metal hydroxide such as sodium hydroxide, potassium hydroxide and lithium hydroxide or ammonium hydroxide.

The precipitate formed by the above procedures is separated by a filtration and is washed and dried to obtain the object compound. When a powder of the object compound should be obtained, the product is washed with water and further washed with an alcohol such as methanol, ethanol and isopropanol especially methanol, and then washed with a ketone such as acetone, methyl ethyl ketone, especially acetone and then, dried to obtain the powder of the object compound.

The reaction is shown by the following reaction formula

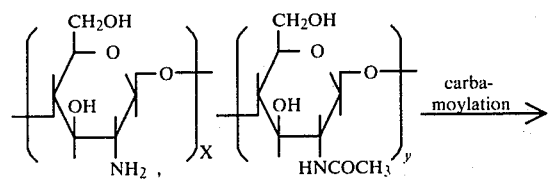

chitosan or its analog

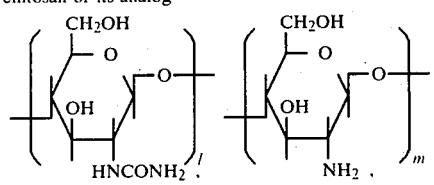

N-carbamoyl-   D-glucos-
D-glucosamine  amine unit
unit

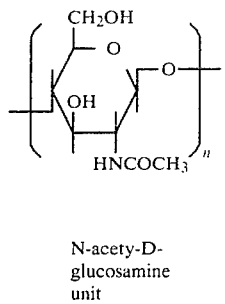

N-acety-D-
glucosamine
unit

The contents of N-carbamoyl-D-glucosamine unit, D-glucosamine unit and N-acetyl-D-glucosamine unit are shown by l, m and n wherein n is given by a degree of residue of acetyl group in chitosan or its analog and l and m can be controlled as desired by selecting the carbamoylation condition.

The resulting product is grayish blue bulk or white powder and is insoluble in water an organic solvent and a base. A solubility of the product in an acid is depending upon the degree of carbamoylation. The detail will be shown in the following examples.

For example, the products obtained by continuing the carbamoylation after the precipitation (Examples 1 to 3) are insoluble in a dilute acid though they are soluble in conc. hydrochloric acid as the same as chitin.

The infrared spectrum of the product has a strong absorption at 1660 cm$^{-1}$ caused by C=O group of a substituted urea but has the other absorptions same as those of the infrared spectrum of chitin. It is confirmed the presence of the N-carbamoyl-D-glucosamine unit from the fact. No absorption peak is found at near 1700 cm$^{-1}$. It is confirmed that the carbamoylation of hydroxyl group of chitosan is not found.

It is also confirmed that the product is a crystalline form by X-ray analysis.

A diffraction pattern of the product is clearly different from the diffraction pattern of chitosan but similar to the diffraction pattern of chitin. The fact is considered to be the similarity of chemical structure of N-carbamoyl-D-glucosamine to that of N-acetyl-D-glucosamine and that of the product obtained by the carbamoylation.

The elementary analysis of the product shows 80% of N-carbamoyl-D-glucosamine unit and 20% of N-acetyl-D-glucosamine which correspond to the contents calculated in the consideration of no D-glucosamine unit. (about 80 to 85% of deacetylation of chitosan as the starting material).

After the precipitation caused by the carbamoylation, i.e. after the carbamoylation of most of amino groups, excess of the agent for carbamoylation is added and the possibility of the carbamoylation of hydroxyl group is studied. Thus, the data of the elementary analysis are substantially equal to those of the former product and no change of the infrared spectrum is found. It is confirmed that any carbamoylation of hydroxyl group is not caused. (Example 2).

It is confirmed from the above-mentioned fact, that in accordance with the process of the present invention, the carbamoylation of only substantially all of amino groups of chitosan can be selectively performed without a blocking of hydroxyl groups under the condition of difference of reactivity of amino group from that of hydroxyl group.

On the other hand, the product obtained by adding a base during the carbamoylation to give 9 of pH of the reaction mixture and separating the precipitate, is swollen in water and dissolved in a dilute acid as a solvent for chitosan. (Example 4).

The infrared spectrum of the product has absorptions at 1660 cm$^{-1}$ and 1560 cm$^{-1}$ and is not different from the infrared spectrum of the former product except that the intensity of the absorption is weak.

It is confirmed that in accordance with the process of the present invention, the contents of N-carbamoyl-D-glucosamine unit and D-glucosamine unit can be varied as desired. The content of the N-acetyl-D-glucosamine unit can be controlled by selecting the degree of deacetylation of chitosan as the starting material. (Examples 5 and 6).

In the reaction of chitosan or its analog with the isocyanic acid, etc., the object compound can be obtained by reacting directly both components as above-mentioned and also it can be obtained by adjusting one or both of the components so as to give a desired form of the object product and if necessary, adding further the component and reacting them under a desired reaction condition.

The N-carbamoyl-D-glucosamine unit resulted by the reaction is called as 2-ureido-2-deoxy-D-glucose that is the glucose-urea derivative. Thus, the polymer having said unit is called as a saccharide derivative having ureido group.

The product is easily decomposed by a microorganism as well as the chitin as the starting material.

The saccharide derivatives having ureido group of the present invention can be used as fabricated products such as films and yarns; an adhesive agent, a bonding agent; a processing agent, a coating agent, a soil improver, a fertilizer coating material, a water swellable material and a water absorbent etc. by utilizing their solubility, crystallizability or biodegradability or a reactivity as the unique reactivity of the amino group of the ureido group different from the other amino groups.

The utilities of the saccharide derivatives having ureido group of the present invention are not limited to said utilities.

The present invention will be further illustrated by certain examples which are provided for purposes of illustration only and are not intended to be limiting the present invention. In the examples, the percent and parts are by weight and the degree of deacetylation of chitosan used in Examples 1 to 4 is in a range of 80 to 85%.

EXAMPLE 1

In 100 wt. parts of deionized water, 0.8 wt. part of chitosan was dispersed and 1.2 wt. parts of acetic acid were added and the mixture was stirred at 19° C. for 10 minutes to dissolve completely chitosan and then, 1.2 wt. parts of sodium isocyanate were added to the solution. The reaction was carried out at 19° C. for 8.5 hours and pH of the reaction mixture was adjusted to 9 with an aqueous solution of sodium carbonate. The precipitate was separated by a filtration and washed with water and then washed with methanol and with acetone and dried to obtain the product. (yield: 0.9 wt. part).

The product obtained by the carbamoylation was a white powder which is insoluble in water, most of organic solvents or a base and also insoluble in an acid except conc. hydrochloric acid.

The infrared spectrum of the product is shown in Table 1 and the infrared spectrum of chitosan as the reference is shown in Table 2.

The infrared spectrum of the product obtained by the carbamoylation had strong absorptions at 1660 cm$^{-1}$ and 1560 cm$^{-1}$ for ureido group. The absorptions were not found in the infrared spectrum of chitosan.

The X-ray diffraction of the product is shown in Table 3. It is confirmed that the product is a crystalline form from Table 3.

The X-ray diffraction pattern of the product is clearly different from that of chitosan but it is similar to that of chitin.

The elementary analysis of the product was as follows. N: 12.10%; C: 37.59%; H: 5.51%. This is substantially the same as the calculated value of the compound having 20% of N-acetyl-D-glucosamine unit and 80% of N-carbamoyl-D-glucosamine unit (N: 12.37%, C: 42.39%; H: 5.99%).

The structure of the product was confirmed from the above-mentioned results.

A mixed solution obtained by adding sodium isocyanate to the aqueous solution of chitosan acetate was coated on a glass plate and kept it under a reduced pressure at 19° C. for 9 hours to prepare a film. The film was peeled off from the glass plate and was dipped into an aqueous solution of sodium carbonate and washed with water and dried. The resulting film was soluble in conc. hydrochloric acid but is insoluble in a dilute acetic acid. The infrared spectrum of the film was substantially the same as that of the product shown in Table 1.

The film is biodegradable and has no toxicity, therefore, it is desirable for disposable films.

Example 2

The accordance with the process of Example 1, the aqueous solution of chitosan acetate was prepared. To the solution, 1.2 wt. parts of sodium isocyanate were added and the mixture was stirred at 20° C. for 30 minutes and then, heated to 70° C. during 1 hour and 15 minutes. To the solution, 0.6 wt. part of acetic acid and 0.8 wt. part of sodium isocyanate were added and the mixture was stirred at 80° C. for 7 hours. The precipitate was separated and washed and dried as set forth in Example 1. (yield: 0.9 wt. part).

The product had the same solubility of the product of Example 1. The infrared spectrum of the product was substantially the same as that shown in Table 1. The X-ray diffraction pattern was substantially the same as that shown in Table 3.

The elementary analysis of the product was as follows and was substantially the same as that of Example 1. N: 12.24%; C: 37.47%; H: 5.62%.

It is confirmed that any carbamoylation of hydroxyl group of chitosan was not resulted.

Example 3

1.5 Wt. parts of 35% hydrochloric acid were diluted with 40 wt. parts of water and 1.6 wt. parts of chitosan was added to the solution and the mixture was stirred at 22° C. for 1 hour to dissolve chitosan and then, 0.7 wt. part of sodium isocyanate was added to react them at 25° C. for 3 hours. The reaction mixture was diluted with 60 wt. parts of water and pH of the reaction mixture was adjusted to 9 with an aqueous solution of sodium hydroxide to form a precipitate. The precipitate was washed and dried as set forth in Example 1. (yield: 1.5 wt. parts).

The product was a white powder which is swollen in dilute acetic acid but is not dissolved in it.

The infrared spectrum of the product was substantially the same as that shown in Table 1 though the intensities of absorptions at 1660 cm$^{-1}$ and 1560 cm$^{-1}$ were weaker than those of Table 1.

The saccharide derivative having ureido group obtained by this process was used as a bonding agent to prepare non-woven fabric of pulp fiber. This was easily decomposed to be suitable as a disposable fabric.

Example 4

In accordance with the process of Example 1, the aqueous solution of chitosan acetate was prepared. To the solution, 1.2 wt. parts of sodium isocyanate were added and the mixture was stirred at 25° C. for 45 minutes and then, pH of the reaction mixture was adjusted to 9 with an aqueous solution of sodium carbonate to form a precipitate. The mixture was further stirred for 5 minutes and then the precipitate was separated and dried as set forth in Example 1.

The product was a white powder which is easily soluble in an aqueous solution of acetic acid.

The infrared spectrum of the product had the absorptions at 1660 cm$^{-1}$ and 1560 cm$^{-1}$ though the intensities of absorptions were weaker than those of Example 3.

An acetic acid solution of the saccharide derivative having ureido group obtained by said process was added to a gypsum slurry to harden the molded mixture. The molded product had higher strength than that of the gypsum product having no addition of said product. The fact shows that the saccharide derivative is effective as a reinforcing agent for gypsum.

Example 5

Chitin powder was isolated from shells of Penaeus (lobster) by the Hackman's method described in R. H. Hackman, Australian J. Bio. Sci., 7 168 (1954). Into 400 wt. parts of 40% aqueous solution of sodium hydroxide, 5 wt. parts of the chitin powder (100-200 mesh) were dispersed, and the mixture was heated at 130° C. for 3 hours under nitrogen gas flow. The product was separated by a filtration, and washed with water and dried to obtain chitosan having 95% of a degree of deacetylation.

In accordance with the process of Example 1, the carbamoylation of the chitosan was carried out.

The product was soluble in conc. hydrochloric acid but was insoluble in dilute acids.

The infrared spectrum of the product was substantially the same as that shown in Table 1. The X-ray diffraction pattern of the product was substantially the same as that shown in Table 3.

The chitosan, acetic acid, sodium isocyanate, and water were mixed at ratios set forth in Example 1. The mixed solution was dipped in a filter paper and kept at 19° C. for 9 hours. Then, the paper was washed with water, with methanol and with acetone and dried. The treated filter paper had less blot of ink and improved strength in comparison with the non-treated filter paper. Therefore, the saccharide derivative having ureido group obtained by said process is suitable as a sizing agent for paper. EXAMPLE 6

Into 75 wt. parts of 40% aqueous solution of sodium hydroxide, 3 wt. parts of chitin powder obtained in the process of Example 5 were dispersed and kept at 25° C.

for 3 hours and then, 225 wt. parts of ice were added and the mixture was stirred to prepare a homogeneous alkaline aqueous solution of alkali chitin. (32% of a degree of deacetylation of a chitin obtained by neutralizing said alkaline aqueous solution of alkali chitin with hydrochloric acid and separating it).

After neutralizing 80 wt. parts of the alkaline aqueous solution of alkali chitin with hydrochloric acid, 0.7 wt. part of 35% hydrochloric acid was added and the mixture was stirred for 10 minutes. Then, 0.5 wt. part of sodium isocyanate was added to the mixture and the reaction was carried out at 4° C. for 24 hours. The pH of the reaction mixture was adjusted to 9 with an aqueous solution of sodium hydroxide and the precipitate was separated by a filtration and washed with water with methanol and then with acetone and dried. (yield: 0.8 wt. part).

The product was a white fibril and was soluble in conc. hydrochloric acid but was insoluble in dilute acids. The product is suitable as a soil improver.

TABLE 1

IR spectrum of carbamoyl chitosan: (100 cm$^{-1}$ ~ 1700 cm$^{-1}$)

| Peak | Intensity |
|---|---|
| 1660 | very strong |
| 1560 | very strong |
| 1420 | shoulder |
| 1380 | medium |
| 1320 | weak |
| 1260 | very weak |
| 1210 | very weak |
| 1160 | strong |
| 1120 | very strong |

TABLE 1-continued

IR spectrum of carbamoyl chitosan: (100 cm$^{-1}$ ~ 1700 cm$^{-1}$)

| Peak | Intensity |
|---|---|
| 1080 | very strong |
| 1040 | very strong |

TABLE 2

IR sprectrum of chitosan: (1000 cm$^{-1}$ ~ 1700 cm$^{-1}$)

| 1640 | weak |
|---|---|
| 1600 | weak |
| 1420 | weak |
| 1380 | medium |
| 1320 | weak |
| 1260 | very weak |
| 1205 | very weak |
| 1160 | strong |
| 1080 | very strong |
| 1030 | very strong |

TABLE 3

X-ray refractory of carbamoyl chitosan:

Peak
$2\theta$ (°) = 9.7, 12.7, 19.7, 26.3

We claim:
1. A macromolecular polysaccharide derived from chitin, having a ureido group, which has 100 to 1% of N-carbamoyl-D-glucosamine unit 0 to 90% of D-glucosamine unit, and 0 to 70% of N-acetyl-D-glucosamine unit.
2. A macromolecular polysaccharide according to claim 1, which has 90 to 30% of N-carbamoyl-D-glucosamine unit, 10 to 70% of D-glucosamine unit, and 10 to 60% of N-acetyl-D-glucosamine unit.

* * * * *